(12) United States Patent
Suda et al.

(10) Patent No.: US 10,583,087 B2
(45) Date of Patent: Mar. 10, 2020

(54) PHARMACEUTICAL COMPOSITION FOR ORAL ADMINISTRATION

(71) Applicant: ASTELLAS PHARMA INC., Tokyo (JP)

(72) Inventors: Yumiko Suda, Tokyo (JP); Toshiro Sakai, Tokyo (JP); Ryo Kojima, Tokyo (JP); Dal Oyama, Tokyo (JP); Koji Nishimura, Tokyo (JP); Kumi Naiki, Tokyo (JP)

(73) Assignee: ASTELLAS PHARMA INC., Tokyo (JP)

(*) Notice: Subject to any disclaimer, the term of this patent is extended or adjusted under 35 U.S.C. 154(b) by 0 days.

(21) Appl. No.: 15/569,682

(22) PCT Filed: Apr. 27, 2016

(86) PCT No.: PCT/JP2016/063151
§ 371 (c)(1),
(2) Date: Oct. 26, 2017

(87) PCT Pub. No.: WO2016/175230
PCT Pub. Date: Nov. 3, 2016

(65) Prior Publication Data
US 2018/0116965 A1 May 3, 2018

(30) Foreign Application Priority Data
Apr. 28, 2015 (JP) .................................. 2015-092005

(51) Int. Cl.
*A61K 9/20* (2006.01)
*A61K 31/497* (2006.01)
*A61K 47/02* (2006.01)
*A61K 47/38* (2006.01)
*A61P 13/02* (2006.01)
*A61P 13/10* (2006.01)

(52) U.S. Cl.
CPC .......... *A61K 9/2054* (2013.01); *A61K 31/497* (2013.01); *A61K 47/02* (2013.01); *A61K 47/38* (2013.01); *A61P 13/02* (2018.01); *A61P 13/10* (2018.01)

(58) Field of Classification Search
CPC .... A61K 9/2054; A61K 31/497; A61K 47/02; A61K 47/38; A61P 13/02; A61P 13/10
See application file for complete search history.

(56) References Cited

U.S. PATENT DOCUMENTS

| 8,673,918 B2* | 3/2014 | Ruegger | A61K 9/0056 514/252.1 |
|---|---|---|---|
| 2002/0031547 A1 | 3/2002 | Takagi et al. | |
| 2007/0254930 A1 | 7/2007 | Ryu et al. | |
| 2013/0143819 A1* | 6/2013 | Torres-Suarez | A61K 9/0056 514/15.2 |
| 2013/0203723 A1 | 8/2013 | Sakuma et al. | |
| 2016/0002218 A1 | 1/2016 | Takahashi et al. | |

FOREIGN PATENT DOCUMENTS

| CN | 101299993 A | 11/2008 |
|---|---|---|
| CN | 103228277 A | 7/2013 |
| JP | 2008-520655 | 6/2008 |
| WO | 1998/29137 A1 | 7/1998 |
| WO | 2007/056205 A2 | 5/2007 |
| WO | 2014/133056 A1 | 9/2014 |

OTHER PUBLICATIONS

Takahashi et al. WO 2014/133056; published: Sep. 4, 2014; English machine translation obtained: Apr. 16, 2018.*
Database Registry on STN, RN: 1624297-26-2; Sep. 2014; paragraph of "Mass Intrinsic Solubility" on table.
Kajiyama, Atsushi, et al; Improvement of HPMC Talbet Disintegration by the Addition of Inorganic Salts, Chem. Pharm. Bull., 2008; vol. 56, No. 4, pp. 598-601; ISSN: 0009-2363, Title, abstract, main text, 1st paragraph, fig. 2, 3, table 1, p. 599, left column, lines 15-18.
Konno, Hajime, et al.; Stabilization Effect of Polymers on Solid Dispersions against Crystallization; Journal of Pharmaceutical Science and Technology; Japan, 2011, vol. 71, No. 2, pp. 109-113; ISSN: 2188-3149, main text, 1st paragraph, p. 109, right column, lines 19-27, fig. 5, 6.
Suzuki, Hideshi et al.; Influence of Water-Soluble Polymers on the Dissolution of Nifedipine Solid Dispersions with Combined Carriers; Chem. Pharm. Bull., 1998; vol. 46, No. 3, pp. 482-487; ISSN: 0009-2363, abstract, main text, 1st paragraph, fig. 1.
Kumprakob, Usanee et al.; Permeation Enhancement of Ketoprofen Using a Supersaturated System with Antinucleant Polymers; Biol. Pharm. Bull., 2005; vol. 28, No. 9; pp. 1684-1688; ISSN: 1347-5215; abstract, fig. 4.
Beak, In-Hwan et al.; Improved Supersaturation and Oral Absorption of Dutasteride by Amorphous Solid Dispersions; Chem. Pharm. Bull.; 2012; vol. 60, No. 11; pp. 1468-1473; ISSN: 0009-2363, abstract, fig. 2.
International Search Report; PCT/JP2016/063151, dated Jul. 13, 2016.
European Patent Office; Communication—Extended European Search Report pursuant to Rule 62 EPC in European Application No. 16786506.2; dated Jan. 3, 2019.
Office Action dated Dec. 20, 2019 in Chinese Patent Application No. 201680024436.1, with English translation.

* cited by examiner

*Primary Examiner* — Johann R Richter
*Assistant Examiner* — Genevieve S Alley
(74) *Attorney, Agent, or Firm* — Kilpatrick Townsend & Stockton LLP (57) ABSTRACT

Disclosed is a pharmaceutical composition for oral administration, comprising 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}pyperidine-4-carboxylic acid, which is a compound having pH-dependent solubility, or a pharmaceutically acceptable salt thereof, and a cellulose derivative. In the pharmaceutical composition for oral administration, the solubility and absorbability of the drug are improved.

8 Claims, 2 Drawing Sheets

Figure 4

PHARMACEUTICAL COMPOSITION FOR ORAL ADMINISTRATION

TECHNICAL FIELD

The present invention relates to a pharmaceutical composition for oral administration, comprising 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}pyperidine-4-carboxylic acid, or a pharmaceutically acceptable salt thereof.

More particularly, the present invention relates to a pharmaceutical composition for oral administration, comprising 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}pyperidine-4-carboxylic acid, or a pharmaceutically acceptable salt thereof, and a cellulose derivative.

BACKGROUND ART

1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}pyperidine-4-carboxylic acid (hereinafter referred to as compound A in some cases) is represented by the following chemical structural formula. Compound A has a muscarinic $M_3$ receptor positive allosteric modulator, and is known to be useful as an agent for preventing and/or treating bladder or urinary tract diseases related to bladder contraction by a muscarinic $M_3$ receptor (Patent literature 1).

[Chem. 1]

In order to improve the disintegration properties of poorly-soluble drugs, a composition comprising a solid dispersion of a drug with a gel-forming water-soluble polymer, and a salt substance that comprises an alkali and a weak or strong acid and has an endothermic standard enthalpy of solution or heat of solution, is known (Patent literature 2).

In order to improve a dissolution rate and bioavailability, an invention, which relates to a rapidly disintegrable pharmaceutical composition which comprises a poorly-soluble drug held on a gel-forming water-soluble polymer as a solid dispersion, wherein it contains a salt substance that comprises an alkali and a weak or strong acid and has an endothermic standard enthalpy of solution or heat of solution, has been proposed (Patent literature 3).

There are some drugs having poor solubility due to not only having simply low solubility but also their properties, such as pH-dependent solubility, or gelation characteristics through contact with water.

Therefore, there is still room for improvement in providing a formulation, in which the dissolution properties of a poorly-soluble drug are improved, and the oral absorbability is improved.

CITATION LIST

Patent Literature

[Patent literature 1] WO 2014/133056
[Patent literature 2] WO 98/29137
[Patent literature 3] Japanese Translation Publication (Kohyo) No. 2008-520655

SUMMARY OF INVENTION

Technical Problem

The inventors focused attention on a pharmaceutical composition comprising compound A or a pharmaceutically acceptable salt thereof, and found that the solubility of compound A was pH-dependent, and that compound A had a problem in which compound A was gelled upon contact with a solvent, such as water.

The fact that the solubility of compound A is pH-dependent, and in particular, that the solubility decreases in a neutral pH range, would cause a possible risk that the compound in a dissolved state would become recrystallized or reprecipitated upon reaching the site of absorption, and as a result, its absorption would decrease.

The fact that compound A is gelled upon contact with a solvent would cause a possible risk that, upon contact with gastric juice or the like in vivo after taking, the drug would be gelled, or a water-soluble polymer as a carrier for a solid dispersion would be gelled and aggregated, and as a result, its absorption would decrease due to the delay of dissolution.

Therefore, in providing the pharmaceutical composition comprising compound A or a pharmaceutically acceptable salt thereof, a pharmaceutical composition capable of being disintegrated before the gelation of compound A or a pharmaceutically acceptable salt thereof, and having good dissolution properties, is desired.

An object of the present invention is to provide a pharmaceutical composition for oral administration, in which the solubility and the absorbability of compound A or a pharmaceutically acceptable salt thereof having pH-dependent solubility is improved.

Solution to Problem

The solubility of compound A in an acidic pH range (first fluid for a dissolution test of the Japanese Pharmacopoeia (JP1 (pH 1.2))) is about 44.1 µg/mL, and the solubility thereof in a neutral pH range (second fluid for a dissolution test of the Japanese Pharmacopoeia (JP2 (pH 6.8))) is about 17.8 µg/mL. Compound A exhibits low solubility in both the acidic pH range and the neutral pH range, and in particular, low solubility in the neutral pH range, and therefore, there is a concern to decrease the dissolution rate in a neutral pH range, such as in the small intestine, and to decrease the bioavailability (BA) due to the delay of dissolution.

Under these circumstances, the inventors focused on the improvement of the solubility and the dissolution properties of compound A, and conducted intensive studies to complete the present invention.

The present invention relates to:

[1] a pharmaceutical composition for oral administration, comprising 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}pyperidine-4-carboxylic acid, or a pharmaceutically acceptable salt thereof, and a cellulose derivative,

[2] the pharmaceutical composition for oral administration of [L], wherein the cellulose derivative is hydroxypropyl cellulose and/or hypromellose,

[3] the pharmaceutical composition for oral administration of [1] or [2], wherein the cellulose derivative is hydroxypropyl cellulose,

[4] the pharmaceutical composition for oral administration of any one of [1] to [3], wherein 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}pyperidine-4-carboxylic acid, or a pharmaceutically acceptable salt thereof, and a cellulose derivative form a solid dispersion,

[5] the pharmaceutical composition for oral administration of any one of [1] to [4], further comprising an effervescent substance,

[6] the pharmaceutical composition for oral administration of [5], wherein the effervescent substance is sodium hydrogen carbonate,

[7] the pharmaceutical composition for oral administration of any one of [1] to [6], further comprising a disintegrating component,

[8] the pharmaceutical composition for oral administration of [7], wherein the disintegrating component is one member or two or more members selected from the group consisting of crystalline cellulose, calcium hydrogen phosphate hydrate, sodium starch glycolate, low-substituted hydroxypropyl cellulose, and croscarmellose sodium,

[9] the pharmaceutical composition for oral administration of [7] or [8], wherein the disintegrating component is one member or two or more members selected from the group consisting of crystalline cellulose, low-substituted hydroxypropyl cellulose, and croscarmellose sodium,

[10] the pharmaceutical composition for oral administration of any one of [7] to [9], wherein the disintegrating component is crystalline cellulose and/or croscarmellose sodium,

[11] the pharmaceutical composition for oral administration of any one of [7] to [10], wherein the disintegrating component is croscarmellose sodium,

[12] the pharmaceutical composition for oral administration of any one of [1] to [11], wherein the content of the cellulose derivative is 10% by weight to 1000% by weight with respect to the weight of 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}pyperidine-4-carboxylic acid, or a pharmaceutically acceptable salt thereof,

[13] the pharmaceutical composition for oral administration of any one of [1] to [12], wherein the pharmaceutical composition for oral administration is a tablet,

[14] the pharmaceutical composition for oral administration of any one of [1] to [13], wherein the pharmaceutical composition for oral administration is a pharmaceutical composition for preventing and/or treating bladder or urinary tract diseases related to bladder contraction by a muscarinic $M_3$ receptor,

[15] a method for improving dissolution properties by an effervescent substance in a pharmaceutical composition for oral administration comprising 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}pyperidine-4-carboxylic acid, or a pharmaceutically acceptable salt thereof, and a cellulose derivative,

[16] use of an effervescent substance for the improvement of dissolution properties in a pharmaceutical composition for oral administration comprising 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}pyperidine-4-carboxylic acid, or a pharmaceutically acceptable salt thereof, and a cellulose derivative.

Advantageous Effects of Invention

According to the pharmaceutical composition for oral administration of the present invention, the pharmaceutical composition comprising compound A or a pharmaceutically acceptable salt thereof, which is gelled upon contact with a solvent, can be rapidly disintegrated and dispersed. Further, a decrease in solubility caused by gelation and aggregation of the drug and/or a water-soluble polymer as a carrier for a solid dispersion can be avoided, and as a result, it can be expected that a decrease in absorbability accompanied by drug crystal precipitation due to a decrease in drug solubility in the small intestine pH range can be avoided.

DESCRIPTION OF EMBODIMENTS

Embodiments of the present invention will be explained in detail hereinafter.

The term "to maintain a supersaturated state" as used herein is defined as a state where, for example, when the following evaluation is carried out in accordance with a Dissolution Test, a paddle method (50 rpm, test fluid: JP2, 250 mL) of the Japanese Pharmacopoeia, the solubility of compound A or a pharmaceutically acceptable salt thereof in the pharmaceutical composition, or the dissolution rate of compound A in the pharmaceutical composition, is 6 times or more (7 times or more in an embodiment) the solubility of compound A or a pharmaceutically acceptable salt thereof in a crystalline state, or the dissolution rate of compound A in a crystalline state, and where the improved state in solubility or the dissolution rate of compound A is maintained for 120 minutes or more.

The term "to improve dissolution properties" as used herein means that the dissolution rate of compound A into water, a buffer, or the like, increases. More particularly, it is defined as a dissolution rate of compound A of 25% or more, preferably 70% or more, and more preferably 85% or more, after 30 minutes from the beginning of a dissolution test of a pharmaceutical composition (for example, a solid dispersion, or a tablet comprising a solid dispersion) comprising compound A or a pharmaceutically acceptable salt thereof, for example, in accordance with a Dissolution Test, a paddle method (25 rpm, test fluid: 0.03 N hydrochloric acid, 900 mL) of the Japanese Pharmacopoeia. Still more preferably, it is defined as a dissolution rate of compound A of 70% or more, and still more preferably 85% or more, after 15 minutes from the beginning of a dissolution test in accordance with a Dissolution Test, a paddle method (50 rpm, test fluid: 0.03 N hydrochloric acid, 900 mL) of the Japanese Pharmacopoeia.

The term "to improve the stability of compound A or a pharmaceutically acceptable salt thereof" as used herein means, when the pharmaceutical composition for oral administration comprising compound A or a pharmaceutically acceptable salt thereof is allowed to stand, "to inhibit the generation of related substances of compound A or a pharmaceutically acceptable salt thereof during storage" or "to inhibit the change in dissolution rate of compound A from the pharmaceutical composition for oral administration."

The term "to inhibit the generation of related substances of compound A or a pharmaceutically acceptable salt thereof during storage" as used herein is defined as an embodiment in which, for example, after the pharmaceutical composition for oral administration is allowed to stand under the conditions described below, a substance having the largest percentage (peak area) among related substances of compound A or a pharmaceutically acceptable salt thereof contained in the pharmaceutical composition for oral administration (maximum related substance), or the total amount of related substances of compound A or a pharmaceutically acceptable salt thereof, is a specific percentage or less.

The percentage of the maximum related substance of compound A or a pharmaceutically acceptable salt thereof is measured, for example, by a high-performance liquid chromatographic method (hereinafter abbreviated as an HPLC method), after storage of the pharmaceutical composition for oral administration at 40° C. and 75% relative humidity (hereinafter abbreviated as % RH) for 1 month under sealed conditions, or after storage thereof at 70° C. for 7 days or 9 days under sealed conditions.

The percentage of the maximum related substance of compound A or a pharmaceutically acceptable salt thereof contained in the pharmaceutical composition for oral administration is defined as 2.0% or less in an embodiment, and 0.9% or less in an embodiment. More particularly, the maximum related substance of compound A or a pharmaceutically acceptable salt thereof is defined as a substance in which, when the peak area of each related substance contained in the pharmaceutical composition for oral administration is measured by an HPLC method, the percentage with respect to the total peak area of compound A or a pharmaceutically acceptable salt thereof and its related substances is the largest.

The total amount of related substances of compound A or a pharmaceutically acceptable salt thereof is measured, for example, by an HPLC method, after storage of the pharmaceutical composition for oral administration at 40° C., 75% RH for 1 month under sealed conditions. The total amount of related substances of compound A or a pharmaceutically acceptable salt thereof contained in the pharmaceutical composition for oral administration is defined as, for example, 3.0% or less, and 1.0% or less in an embodiment.

As the conditions for a stability test, instead of the above-mentioned storage for 1 month at 40° C., 75% RH under opened conditions, storage for 2 months, 3 months, or 6 months under the same conditions may be used. Further, storage at 25° C., 60% RH under opened conditions for 1 month to 24 months, or to 36 months may be appropriately selected. Furthermore, it may be evaluated, for example, at 70° C. for 7 days or 9 days (opened, or sealed in a bottle), so that the evaluation can be carried out for a short time. In this case, with respect to evaluation of "to be stable" as used herein, for example, a method that is judged to be scientifically valid, such as an extrapolation method, may be used, so that the conditions thermodynamically correspond to the result under storage conditions at 40° C. for 6 months.

The term "to inhibit the change in dissolution rate of compound A from a pharmaceutical composition for oral administration" as used herein means to decrease the change in the dissolution rate of compound A from a pharmaceutical composition for oral administration, more particularly, to decrease the difference between the dissolution rate after storage and the dissolution rate before storage. It means that, for example, when the pharmaceutical composition for oral administration is allowed to stand at 25° C., 75% RH for 6 days under opened conditions, and a dissolution test is carried out in accordance with a Dissolution Test, a paddle method (50 rpm, test fluid: 0.03 N hydrochloric acid, 900 mL) of the Japanese Pharmacopoeia, the change in dissolution rate (the difference between the dissolution rate after storage and the dissolution rate before storage) after 30 minutes from the beginning of the test is 10% or less before and after storage, and the change in the dissolution rate after 15 minutes from the beginning of the test is 10% or less before and after storage in an embodiment. Further, it means that, when the pharmaceutical composition for oral administration is allowed to stand at 25° C., 75% RH for 21 days under opened conditions, and a dissolution test is carried out in accordance with a Dissolution Test, a paddle method (50 rpm, test fluid: 0.03 N hydrochloric acid, 900 mL) of the Japanese Pharmacopoeia, the change in the dissolution rate (the difference between the dissolution rate after storage and the dissolution rate before storage) after 30 minutes from the beginning of the test is 10% or less before and after storage.

The pharmaceutical composition for oral administration of the present invention will be explained in detail hereinafter.

Compound A or a pharmaceutically acceptable salt thereof, which is used in the present invention, is easily available, for example, by a method described in Patent literature 1, or in a similar fashion to that.

Compound A may be in a free form in an embodiment, and may form a pharmaceutically acceptable salt with an acid or a base in other embodiments. Examples of such a salt include an acid addition salt with an inorganic acid, such as hydrochloric acid, hydrobromic acid, hydroiodic acid, sulfuric acid, nitric acid, phosphoric acid, or the like; an acid addition salt with an organic acid, such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, amino acid, or the like; a salt with an inorganic base, such as sodium, potassium, magnesium, calcium, aluminum, or the like; a salts with an organic base, such as methylamine, ethylamine, ethanolamine, or the like; a salt with an amino acid or a derivative thereof, such as acetylleucine, lysine, ornithine, or the like; and ammonium salt, or the like.

These salts can be prepared by conventional methods.

For ordinary oral administration, the daily dosage is suitably about 0.001 to 100 mg/kg per body weight. This is administered in one dose, or divided into two to four doses per day. The dose may be appropriately determined according to individual cases in consideration of the symptoms, age, sex, and the like.

The content of compound A or a pharmaceutically acceptable salt thereof is, for example, per pharmaceutical composition, 1% by weight or more and 70% by weight or less in an embodiment, 5% by weight or more and 70% by weight or less in an embodiment, 5% by weight or more and 50% by weight or less in an embodiment, 5% by weight or more and 20% by weight or less in an embodiment, and 10% by weight or more and 15% by weight or less in an embodiment.

The cellulose derivative, which is used in the present invention, is not particularly limited, so long as the solubility of compound A is 6 times or more that of compound A or a pharmaceutically acceptable salt thereof in a crystalline state. Examples of the cellulose derivative include hypromellose and hydroxypropyl cellulose (hereinafter abbreviated as HPC in some cases). Examples of hypromellose include TC—5E and TC—5R (manufactured by Shin-Etsu Chemical Co., Ltd.). Examples of HPC include HPC—L and HPC—SL (manufactured by Nippon Soda Co., Ltd.).

These cellulose derivatives can be used alone, or as an appropriate combination of two or more.

The content of the cellulose derivative is not particularly limited, so long as the solubility of compound A is 6 times or more that of compound A or a pharmaceutically acceptable salt thereof in a crystalline state. The content is, for example, with respect to the weight of the pharmaceutical composition, 0.1% by weight or more and 75% by weight or less in an embodiment, 0.5% by weight or more and 35% by weight or less in an embodiment, and 1% by weight or more and 10% by weight or less in an embodiment. The content is, with respect to the weight of compound A or a pharmaceutically acceptable salt thereof, 10% by weight or more and 1000% by weight or less in an embodiment, 20% by weight or more and 500% by weight or less in an embodiment, 30% by weight or more and 40% by weight or less in an embodiment, and 35% by weight in an embodiment.

The effervescent substance, which is used in the present invention, is not particularly limited, so long as it can foam in water, a buffer, or gastric juice.

Examples of the effervescent substance include sodium hydrogen carbonate.

The content of the effervescent substance is not particularly limited, so long as it can foam in liquid, such as gastric juice, water, or a buffer. The content is, for example, with respect to the weight of the pharmaceutical composition, 0.1% by weight or more and 90% by weight or less in an embodiment, 1% by weight or more and 60% by weight or less in an embodiment, 1% by weight or more and 40% by weight or less in an embodiment, and 2% by weight or more and 30% by weight or less in an embodiment. The content is, with respect to the weight of compound A or a pharmaceutically acceptable salt thereof, 10% by weight or more and 300% by weight or less in an embodiment, 20% by weight or more and 250% by weight or less in an embodiment, 30% by weight or more and 250% by weight or less in an embodiment, and 30% by weight or more and 200% by weight or less in an embodiment.

The disintegrating component, which is used in the present invention, is not particularly limited, so long as it is a water-insoluble substance or a water swellable substance, and it can improve the disintegration properties of the pharmaceutical composition for oral administration of the present invention, and/or the dissolution properties of compound A.

Examples of the disintegrating component include crystalline cellulose, calcium hydrogen phosphate hydrate, sodium starch glycolate, low-substituted hydroxypropyl cellulose, croscarmellose sodium, and the like. The disintegrating component is preferably crystalline cellulose, low-substituted hydroxypropyl cellulose, or croscarmellose sodium, more preferably crystalline cellulose or croscarmellose sodium, and still more preferably croscarmellose sodium.

These disintegrating components can be used alone, or as an appropriate combination of two or more.

The content of the disintegrating components is not particularly limited, so long as it can improve the disintegration properties of the pharmaceutical composition for oral administration of the present invention, and/or the dissolution properties of compound A. The content is, for example, with respect to the weight of the pharmaceutical composition, 1% by weight or more and 99% by weight or less in an embodiment, and 5% by weight or more and 80% by weight or less in an embodiment. The content is, with respect to the weight of compound A or a pharmaceutically acceptable salt thereof, 10% by weight or more and 1000% by weight or less in an embodiment, 35% by weight or more and 600% by weight or less in an embodiment, and 50% by weight or more and 600% by weight or less in an embodiment.

The total content of the effervescent substance and the disintegrating component is not particularly limited, so long as it can improve the stability of compound A or a pharmaceutically acceptable salt thereof, and/or the dissolution stability of compound A. It is, for example, with respect to the weight of the pharmaceutical composition, 10% by weight or more and 60% by weight or less in an embodiment, 15% by weight or more and 50% by weight or less in an embodiment, and 25% by weight or more and 40% by weight or less in an embodiment, In the pharmaceutical composition for oral administration of the present invention, it may be formulated by appropriately using various pharmaceutical additives, if desired, to the extent that the desired effects of the present invention can be achieved. Such pharmaceutical additives are not particularly limited, so long as they are pharmaceutically acceptable and pharmacologically acceptable. Examples of the pharmaceutical additives include a filler, a binder, an acidulant, a sweetener, a flavor, a colorant, a buffering agent, an antioxidant, a surfactant, and the like.

Examples of the filler include starch, pregelatinized starch, dextrin, sodium carboxymethylcellulose, gum arabic, dextrin, pullulan, light anhydrous silicic acid, synthetic aluminum silicate, magnesium metasilicate aluminate, and the like.

Examples of the binder include gum arabic, hydroxyethyl cellulose, and the like.

Examples of the acidulant include citric acid, tartaric acid, malic acid, and the like.

Examples of the sweetener include saccharin sodium, glycyrrhizic acid, aspartame, stevia, thaumatin, and the like.

Examples of the flavor include lemon, lime, orange, menthol, and the like.

Examples of the colorant include food yellow No. 4, food yellow No. 5, food red No. 3, food red No. 102, food blue No. 3, and the like.

Examples of the buffering agent include citric acid, succinic acid, fumaric acid, tartaric acid, ascorbic acid or salts thereof, glutamic acid, glutamine, glycine, aspartic acid, alanine, arginine or salts thereof, magnesium oxide, zinc oxide, magnesium hydroxide, phosphoric acid, boric acid or salts thereof, and the like.

Examples of the antioxidant include ascorbic acid, dibutylhydroxytoluene, propyl gallate, and the like.

Examples of the surfactant include polysorbate 80, sodium lauryl sulfate, polyoxyethylene hydrogenated castor oil, and the like.

These pharmaceutical additives may be appropriately added alone, or as a combination of two or more, in appropriate amounts.

With respect to the content of each pharmaceutical additive, it may be used within the range where the desired effects of the present invention can be achieved.

The method of producing the pharmaceutical composition for oral administration of the present invention will be explained in detail hereinafter.

The pharmaceutical composition for oral administration of the present invention may be produced by appropriately combining known methods per se.

(1) Solid Dispersion Preparation Step:

The solid dispersion, an embodiment of the pharmaceutical composition for oral administration of the present invention, may be produced by dissolving and/or suspending compound A or a pharmaceutically acceptable salt thereof and a cellulose derivative in a pharmaceutically acceptable solvent, and evaporating the solvent.

The solvent, which is used in the present invention, is not particularly limited, so long as the cellulose derivative, and compound A or a pharmaceutically acceptable salt thereof can be dissolved and/or suspended. Examples of the solvent include ketones, such as acetone; alcohols, such as methanol, ethanol, or propanol; dichloromethane; and a mixed solvent thereof, or a mixed solvent thereof with water. The pharmaceutically acceptable solvents may be used alone, or as an appropriate combination of two or more.

The method of evaporating the pharmaceutically acceptable solvent, which is used in the present invention, is not particularly limited, so long as the solvent can be removed from the liquid in which compound A or a pharmaceutically acceptable salt thereof and the water-soluble polymer are dissolved and/or suspended. Examples of the evaporation method include spray drying, drying under reduced pressure, forced-air drying, and the like; and include spray drying in an embodiment.

(2) Granulation Step:

In the granulation step, an apparatus and a method are not particularly limited, so long as the drug and the like may be granulated.

Examples of the production method and the apparatus include a fluidized bed granulation method, a melting granulation method, a high shear granulation method, a milling (pulverization) and granulation method, an extrusion granulation method, a tumbling granulation method, a spray granulation method, and a dry granulation method; and apparatuses and the like, which are used in these methods. They are a dry granulation method and a dry granulator in an embodiment.

The binders for the granulation methods may be used alone, or as an appropriate combination of two or more.

After the granulation, the granulated product may be dried. The drying method is not particularly limited, so long as it is a method capable of conventionally and pharmaceutically drying the granulated product.

The granulated product prepared as above may be used to prepare various formulations, such as tablets, capsules, powders, granules, dry syrups, or the like. The pharmaceutical composition for oral administration of the present invention is a tablet in an embodiment.

(3) Molding Step:

In the molding step, an apparatus and a method are not particularly limited, so long as it is a method for molding the pharmaceutical composition for oral administration of the present invention. Examples of the method include a method of producing a tablet by mixing the drug in the present invention or the solid dispersion of the present invention with appropriate pharmaceutical additives, and directly compression-molding the mixture, without the granulation and drying step; a method of producing a tablet by carrying out granulation, mixing the obtained product with a lubricant, and compression-molding the mixture; and the like.

Examples of a tableting machine include a rotary tableting machine, an oil press, and the like.

The conditions for tableting, such as tableting pressure, are not particularly limited, so long as it is tableting pressure capable of producing tablets.

The hardness of the tableted product is not particularly limited, so long as it is not damaged during the manufacturing process, the distribution process, and the like. The hardness may be, for example, 40 to 500 N.

(4) Film Coating Step:

After tableting, the surface of the tablets may be film coated.

The method of film coating is not particularly limited, so long as the tablets may be conventionally and pharmaceutically coated. Examples of the coating include pan coating, dip coating, and the like.

The coating rate is not particularly limited, so long as a film can be formed. The coating rate is, for example, with respect to the total weight of the formulation, 1% by weight to 10% by weight, or the like.

After film coating, the obtained film coated tablets may be dried. The drying method is not particularly limited, so long as the film coated tablets can be conventionally and pharmaceutically dried. The conditions for drying are not particularly limited, so long as they are appropriately selected in view of, for example, the stability of the formulation.

The pharmaceutical composition for oral administration of the present invention is used, for example, as a pharmaceutical composition for preventing and/or treating bladder or urinary tract diseases related to bladder contraction by a muscarinic $M_3$ receptor.

The method of producing the pharmaceutical composition for oral administration of the present invention includes, in addition to the above-mentioned method, a production method comprising an appropriate combination of known methods per se.

The present invention includes a method for improving dissolution properties by an effervescent substance in a pharmaceutical composition for oral administration comprising compound A or a pharmaceutically acceptable salt thereof, and a cellulose derivative.

With respect to "compound A or a pharmaceutically acceptable salt thereof" and the "cellulose derivative", which are used in the method for improving dissolution properties of the present invention, the explanations therefor described in the pharmaceutical composition for oral administration of the present invention can be directly applied.

According to the method for improving dissolution properties of the present invention, in providing the pharmaceutical composition for oral administration comprising compound A or a pharmaceutically acceptable salt thereof and a cellulose derivative, the dissolution properties of compound A can be improved by adding the effervescent substance to the pharmaceutical composition.

With respect to the content of each component in the method for improving dissolution properties of the present invention, the explanations therefor described in the pharmaceutical composition for oral administration of the present invention and the method of producing the same can be directly applied.

The present invention includes a use of an effervescent substance for the improvement of dissolution properties in a pharmaceutical composition for oral administration comprising compound A or a pharmaceutically acceptable salt thereof, and a cellulose derivative.

With respect to the "pharmaceutical composition for oral administration comprising compound A or a pharmaceutically acceptable salt thereof, and a cellulose derivative" and the "effervescent substance", which are used in the present invention, the explanations therefor described in the pharmaceutical composition for oral administration of the present invention can be directly applied.

According to the use of the effervescent substance of the present invention, in providing the pharmaceutical composition for oral administration comprising compound A or a pharmaceutically acceptable salt thereof and a cellulose derivative, the dissolution properties can be improved.

With respect to the content of each component and their blending method in the use of the present invention, the explanations therefor described in the pharmaceutical composition for oral administration of the present invention and the method of producing the same can be directly applied.

EXAMPLES

Compound A, which was used in the Examples or the like below, had been prepared in accordance with a method described in WO 2014/133056.

The present invention will now be further illustrated by, but is by no means limited to, the following Examples and Experimental Examples.

Example 1

In accordance with the formulation as shown in Table 1, 0.5 g of compound A and 1.5 g of hypromellose (TC—5E, manufactured by Shin-Etsu Chemical Co., Ltd., unless otherwise stated, the same compound was used in the following) were dissolved in a mixture of dichloromethane and methanol to prepare a spray solution. The spray solution was dried by spray-drying to obtain a pharmaceutical composition for oral administration (solid dispersion) of the present invention.

Example 2

In accordance with the formulation as shown in Table 1, 0.5 g of compound A and 1.5 g of hydroxypropyl cellulose (HPC-SL, manufactured by Nippon Soda Co., Ltd., unless otherwise stated, the same compound was used in the following) were dissolved in a mixture of dichloromethane and methanol to prepare a spray solution. The spray solution was dried by spray-drying to obtain a pharmaceutical composition for oral administration (solid dispersion) of the present invention.

Comparative Example 1

In accordance with the formulation as shown in Table 1, 0.5 g of compound A and 1.5 g of polyvinylpyrrolidone (Kollidon30, manufactured by BASF) were dissolved in a mixture of dichloromethane and methanol to prepare a spray solution. The spray solution was dried by spray-drying to obtain a pharmaceutical composition for oral administration (solid dispersion) for comparison.

Example 3

(1) Preparation of Solid Dispersion

A spray solution was prepared by dissolving 250.0 g of compound A and 87.5 g of hydroxypropyl cellulose in a mixture of dichloromethane and methanol. The spray solution was dried by spray-drying to obtain a pharmaceutical composition for oral administration (solid dispersion) of the present invention.

(2) Molding 1350 mg of the solid dispersion prepared in (1), 1500 mg of sodium hydrogen carbonate (sodium hydrogen carbonate, manufactured by Merck, unless otherwise stated, the same compound was used in the following), 3075 mg of crystalline cellulose (Ceolus PH-101, manufactured by Asahi Kasei Chemicals Corporation, unless otherwise stated, the same compound was used in the following), 1500 mg of sodium starch glycolate (Primojel, manufactured by DMV-Fonterra, unless otherwise stated, the same compound was used in the following), and 75 mg of magnesium stearate (Parteck (registered trademark) LUB MST, manufactured by MERCK, unless otherwise stated, the same compound was used in the following) were mixed. A pharmaceutical composition for oral administration (tablet) of the present invention was obtained by compression-molding 750 mg of the mixture. The formulation is shown in Table 1.

Example 4

(1) Preparation of Solid Dispersion

A spray solution was prepared by dissolving 1200 g of compound A and 420 g of hydroxypropyl cellulose in a mixture of dichloromethane and methanol. The spray solution was dried by spray-drying to obtain a pharmaceutical composition for oral administration (solid dispersion) of the present invention.

(2) Molding 1350 mg of the solid dispersion prepared in (1), 1500 mg of sodium hydrogen carbonate, 3131.25 mg of crystalline cellulose, 1500 mg of sodium starch glycolate, and 18.75 mg of magnesium stearate were mixed. A pharmaceutical composition for oral administration (tablet) of the present invention was obtained by compression-molding 750 mg of the mixture. The formulation is shown in Table 1.

Example 5

675 mg of the solid dispersion prepared in Example 3(1), 375 mg of sodium hydrogen carbonate, 1912.5 mg of crystalline cellulose, 750 mg of sodium starch glycolate, and 37.5 mg of magnesium stearate were mixed. 750 mg of the mixture was weighed and compression-molded to obtain a pharmaceutical composition for oral administration (tablet) of the present invention. The formulation is shown in Table 1.

Example 6

675 mg of the solid dispersion prepared in Example 3(1), 187.5 mg of sodium hydrogen carbonate, 2100 mg of crystalline cellulose, 750 mg of sodium starch glycolate, and 37.5 mg of magnesium stearate were mixed. 750 mg of the mixture was weighed and compression-molded to obtain a pharmaceutical composition for oral administration (tablet) of the present invention. The formulation is shown in Table 2.

Example 7

675 mg of the solid dispersion prepared in Example 3(1), 750 mg of sodium hydrogen carbonate, 1537.5 mg of calcium hydrogen phosphate hydrate (rika, manufactured by Kyowa Chemical Industry Co., Ltd.), 750 mg of sodium starch glycolate, and 37.5 mg of magnesium stearate were mixed. 750 mg of the mixture was weighed and compression-molded to obtain a pharmaceutical composition for oral administration (tablet) of the present invention. The formulation is shown in Table 2.

Example 8

1350 mg of the solid dispersion prepared in Example 4(1), 1500 mg of sodium hydrogen carbonate, 3131.25 mg of crystalline cellulose, 1500 mg of low-substituted hydroxypropyl cellulose (L-HPC LH11, manufactured by Shin-Etsu Chemical Co., Ltd.), and 18.75 mg of magnesium stearate were mixed. 750 mg of the mixture was weighed and compression-molded to obtain a pharmaceutical composition for oral administration (tablet) of the present invention. The formulation is shown in Table 2.

Example 9

2700 mg of the solid dispersion prepared in Example 4(1), 3000 mg of sodium hydrogen carbonate, 6262.5 mg of crystalline cellulose, 3000 mg of croscarmellose sodium (KICCOLATE ND—2HS, manufactured by Nichirin Chemical Industries, Ltd.), and 37.5 mg of magnesium stearate were mixed. 750 mg of the mixture was weighed and compression-molded to obtain a pharmaceutical composition of the present invention. The formulation is shown in Table 2.

Example 10

(1) Preparation of Solid Dispersion

A spray solution was prepared by dissolving 2.0 kg of compound A and 0.7 kg of hydroxypropyl cellulose in a mixture of dichloromethane and methanol. The spray solution was dried by spray-drying to obtain a pharmaceutical composition for oral administration (solid dispersion) of the present invention.

(2) Granulation and Molding 2700 g of the solid dispersion prepared in (1), 3000 g of sodium hydrogen carbonate, 6262.5 g of crystalline cellulose, and 3000 g of sodium starch glycolate were mixed and dry-granulated. 37.5 g of magnesium stearate was further mixed and compression-molded. The molded product was film-coated with 450 g of a film coating agent (OPADRY, manufactured by Colorcon, unless otherwise stated, the same compound was used in the following) to obtain a pharmaceutical composition for oral administration (tablet) of the present invention. The formulation is shown in Table 2.

Example 11

378.0 g of the solid dispersion prepared under the same conditions as those in Example 10(1), 420.0 g of sodium hydrogen carbonate, 876.75 g of crystalline cellulose, and 420.0 g of sodium starch glycolate were mixed and dry-granulated. 5.25 g of magnesium stearate was further mixed and compression-molded. The molded product was film-coated with 63 g of a film coating agent to obtain a pharmaceutical composition for oral administration (tablet) of the present invention. The formulation is shown in Table 2.

TABLE 1

|  | Example 1 | Example 2 | Comp. Example 1 | Example 3 | Example 4 | Example 5 |
|---|---|---|---|---|---|---|
| Compound A | 100 | 100 | 100 | 100 | 100 | 100 |
| Hypromellose | 300 | — | — | — | — | — |
| Hydroxypropyl cellulose | — | 300 | — | 35 | 35 | 35 |
| Polyvinyl-pyrrolidone | — | — | 300 | — | — | — |
| Sodium hydrogen carbonate | — | — | — | 150 | 150 | 75 |
| Crystalline cellulose | — | — | — | 307.5 | 313.125 | 382.5 |
| Sodium starch glycolate | — | — | — | 150 | 150 | 150 |
| Magnesium stearate | — | — | — | 7.5 | 1.875 | 7.5 |
| Total amount | 400 | 400 | 400 | 750 | 750 | 750 |

Unit: mg

TABLE 2

|  | Example 6 | Example 7 | Example 8 | Example 9 | Example 10 | Example 11 |
|---|---|---|---|---|---|---|
| Compound A | 100 | 100 | 100 | 100 | 100 | 10 |
| Hydroxypropyl cellulose | 35 | 35 | 35 | 35 | 35 | 3.5 |
| Sodium hydrogen carbonate | 37.5 | 150 | 150 | 150 | 150 | 15 |
| Crystalline cellulose | 420 | — | 313.125 | 313.125 | 313.125 | 31.3125 |
| Calcium hydrogen phosphate hydrate | — | 307.5 | — | — | — | — |

TABLE 2-continued

|  | Example 6 | Example 7 | Example 8 | Example 9 | Example 10 | Example 11 |
|---|---|---|---|---|---|---|
| Sodium starch glycolate | 150 | 150 | — | — | 150 | 15 |
| Low-substituted hydroxypropyl cellulose | — | — | 150 | — | — | — |
| Croscarmellose sodium | — | — | — | 150 | — | — |
| Magnesium stearate | 7.5 | 7.5 | 1.875 | 1.875 | 1.875 | 0.1875 |
| Film coating agent | — | — | — | — | 22.5 | 2.25 |
| Total amount | 750 | 750 | 750 | 750 | 772.5 | 77.25 |

Unit: mg

Example 12

2700 mg of the solid dispersion prepared in Example 4(1), 750 mg of sodium hydrogen carbonate, 8512.5 mg of crystalline cellulose, 3000 mg of croscarmellose sodium, and 37.5 mg of magnesium stearate were mixed. 750 mg of the mixture was weighed and compression-molded to obtain a pharmaceutical composition for oral administration (tablet) of the present invention. The formulation is shown in Table 3.

Example 13

1350 mg of the solid dispersion prepared in Example 4(1), 750 mg of sodium hydrogen carbonate, 4256.25 mg of crystalline cellulose, 1125 mg of croscarmellose sodium, and 18.75 mg of magnesium stearate were mixed. 750 mg of the mixture was weighed and compression-molded to obtain a pharmaceutical composition for oral administration (tablet) of the present invention. The formulation is shown in Table 3.

Example 14

2700 mg of the solid dispersion prepared in Example 4(1), 1500 mg of sodium hydrogen carbonate, 7762.5 mg of crystalline cellulose, 3000 mg of croscarmellose sodium, and 37.5 mg of magnesium stearate were mixed. 750 mg of the mixture was weighed and compression-molded to obtain a pharmaceutical composition for oral administration (tablet) of the present invention. The formulation is shown in Table 3.

Example 15

1350 mg of the solid dispersion prepared in Example 4(1), 937.5 mg of sodium hydrogen carbonate, 4256.25 mg of crystalline cellulose, 937.5 mg of croscarmellose sodium, and 18.75 mg of magnesium stearate were mixed. 750 mg of the mixture was weighed and compression-molded to obtain a pharmaceutical composition for oral administration (tablet) of the present invention. The formulation is shown in Table 3.

Example 16

1350 mg of the solid dispersion prepared in Example 4(1), 1125 mg of sodium hydrogen carbonate, 4256.25 mg of crystalline cellulose, 750 mg of croscarmellose sodium, and 18.75 mg of magnesium stearate were mixed. 750 mg of the mixture was weighed and compression-molded to obtain a pharmaceutical composition for oral administration (tablet) of the present invention. The formulation is shown in Table 3.

Example 17

1350 mg of the solid dispersion prepared in Example 4(1), 1125 mg of sodium hydrogen carbonate, 3881.25 mg of crystalline cellulose, 1125 mg of croscarmellose sodium, and 18.75 mg of magnesium stearate were mixed. 750 mg of the mixture was weighed and compression-molded to obtain a pharmaceutical composition for oral administration (tablet) of the present invention. The formulation is shown in Table 3.

Example 18

2700 mg of the solid dispersion prepared in Example 4(1), 3000 mg of sodium hydrogen carbonate, 8512.5 mg of crystalline cellulose, 750 mg of croscarmellose sodium, and 37.5 mg of magnesium stearate were mixed. 750 mg of the mixture was weighed and compression-molded to obtain a pharmaceutical composition for oral administration (tablet) of the present invention. The formulation is shown in Table 3.

Example 19

2700 mg of the solid dispersion prepared in Example 4(1), 3000 mg of sodium hydrogen carbonate, 7762.5 mg of crystalline cellulose, 1500 mg of croscarmellose sodium, and 37.5 mg of magnesium stearate were mixed. 750 mg of the mixture was weighed and compression-molded to obtain a pharmaceutical composition for oral administration (tablet) of the present invention. The formulation is shown in Table 3.

Example 20

2700 mg of the solid dispersion prepared in Example 4(1), 4500 mg of sodium hydrogen carbonate, 7012.5 mg of crystalline cellulose, 750 mg of croscarmellose sodium, and 37.5 mg of magnesium stearate were mixed. 750 mg of the mixture was weighed and compression-molded to obtain a pharmaceutical composition for oral administration (tablet) of the present invention. The formulation is shown in Table 3.

Example 21

2700 mg of the solid dispersion prepared in Example 4(1), 750 mg of sodium hydrogen carbonate, 10012.5 mg of crystalline cellulose, 1500 mg of croscarmellose sodium, and 37.5 mg of magnesium stearate were mixed. 750 mg of the mixture was weighed and compression-molded to obtain a pharmaceutical composition for oral administration (tablet) of the present invention. The formulation is shown in Table 3.

Example 22

2700 mg of the solid dispersion prepared in Example 4(1), 1500 mg of sodium hydrogen carbonate, 9262.5 mg of crystalline cellulose, 1500 mg of croscarmellose sodium, and 37.5 mg of magnesium stearate were mixed. 750 mg of the mixture was weighed and compression-molded to obtain a pharmaceutical composition for oral administration (tablet) of the present invention. The formulation is shown in Table 3.

TABLE 3

|  | Example 12 | Example 13 | Example 14 | Example 15 | Example 16 |
|---|---|---|---|---|---|
| Compound A | 100 | 100 | 100 | 100 | 100 |
| Hydroxypropyl cellulose | 35 | 35 | 35 | 35 | 35 |
| Sodium hydrogen carbonate | 37.5 | 75 | 75 | 93.75 | 112.5 |
| Crystalline cellulose | 425.625 | 425.625 | 388.125 | 425.625 | 425.625 |
| Croscarmellose sodium | 150 | 112.5 | 150 | 93.75 | 75 |
| Magnesium stearate | 1.875 | 1.875 | 1.875 | 1.875 | 1.875 |
| Total amount | 750 | 750 | 750 | 750 | 750 |

|  | Example 17 | Example 18 | Example 19 | Example 20 | Example 21 | Example 22 |
|---|---|---|---|---|---|---|
| Compound A | 100 | 100 | 100 | 100 | 100 | 100 |
| Hydroxypropyl cellulose | 35 | 35 | 35 | 35 | 35 | 35 |
| Sodium hydrogen carbonate | 112.5 | 150 | 150 | 225 | 37.5 | 75 |
| Crystalline cellulose | 388.125 | 425.625 | 388.125 | 350.625 | 500.625 | 463.125 |
| Croscarmellose sodium | 112.5 | 37.5 | 75 | 37.5 | 75 | 75 |
| Magnesium stearate | 1.875 | 1.875 | 1.875 | 1.875 | 1.875 | 1.875 |
| Total amount | 750 | 750 | 750 | 750 | 750 | 750 |

Unit: mg

<Experimental Example 1> Supersaturation Test

With respect to the pharmaceutical compositions for oral administration (solid dispersions) of Examples 1 and 2 and Comparative Example 1, 664 mg was weighed and suspended in water to prepare suspensions of 1.33 mg/mL. Immediately after the preparation, these samples were subjected to a dissolution test, and evaluated. The test was carried out under the following dissolution test conditions:

JP2, 250 mL;

Paddle method, 50 rpm; and

Ultraviolet spectroscopy (UV method (measurement wavelength: 348 nm))

Figure 1:
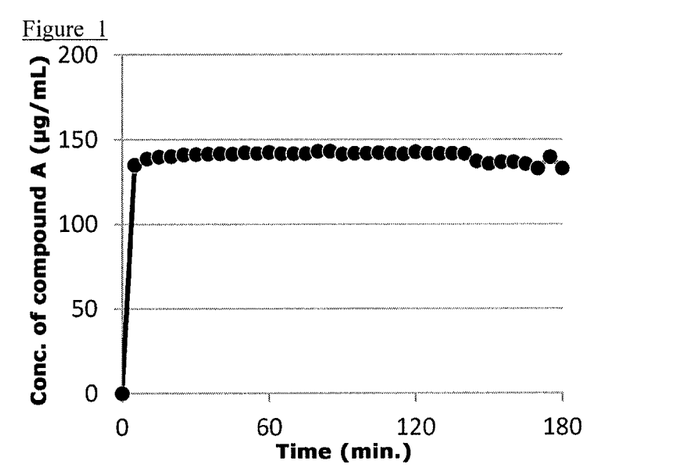
FIG. 1 is a graph showing the results of a supersaturation test of the pharmaceutical composition for oral administration of Example 1.
Figure 2:
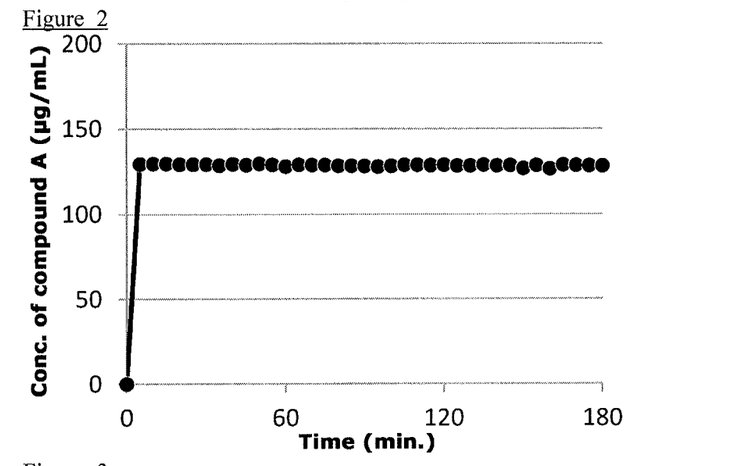
FIG. 2 is a graph showing the results of a supersaturation test of the pharmaceutical composition for oral administration of Example 2.
Figure 3:
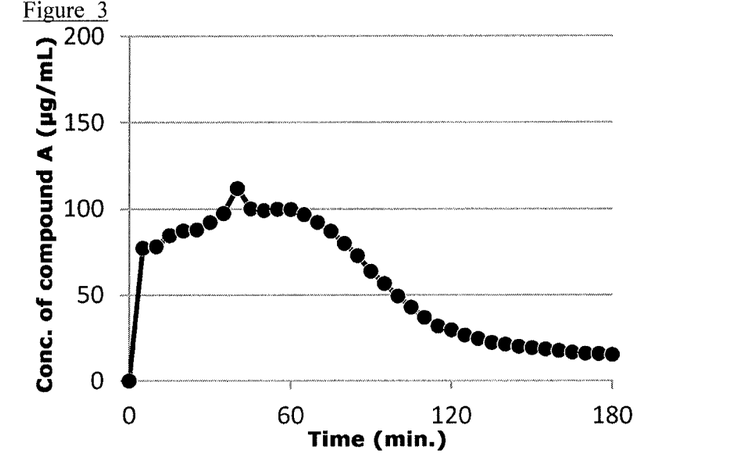
FIG. 3 is a graph showing the results of a supersaturation test of the pharmaceutical composition for oral administration of Comparative Example 1.

The results are shown in FIGS. 1 to 3. In the solid dispersion using polyvinylpyrrolidone (FIG. 3, Comparative Example 1), the decrease in the dissolution rate was observed after 60 minutes. On the other hand, a supersaturated state was maintained in the solid dispersion using hypromellose (FIG. 1, Example 1) and the solid dispersion using hydroxypropyl cellulose (FIG. 2, Example 2).

<Experimental Example 2> Measurement of Dissolution Rate

Figure 4:
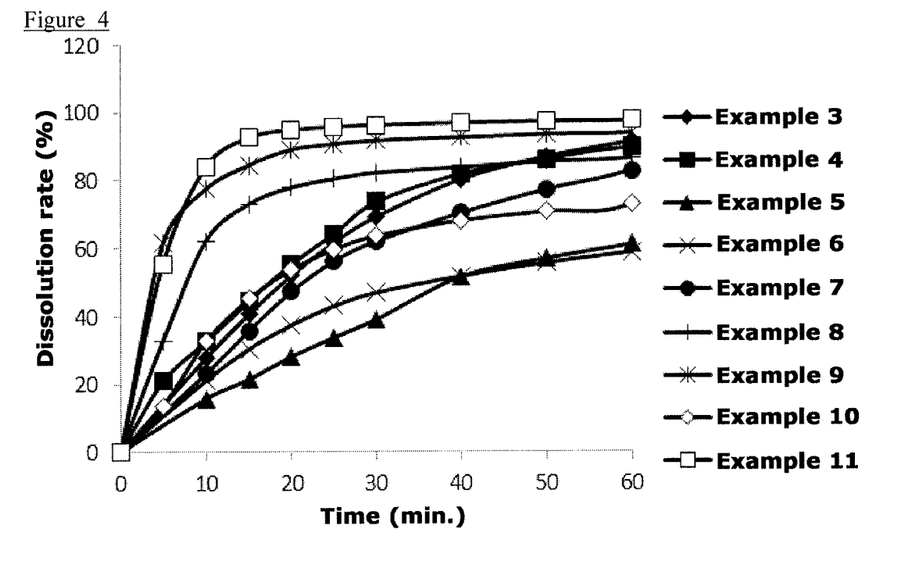
FIG. 4 is a graph showing the results of a dissolution rate measurement of the pharmaceutical compositions for oral administration of Examples 3 to 11.

With respect to the pharmaceutical compositions for oral administration (tablets) of Examples 3 to 11, the dissolution rate was measured in accordance with a Dissolution Test, a paddle method (25 rpm) of the Japanese Pharmacopoeia. As a test fluid, 0.03 N hydrochloric acid (900 mL) was used, and the measurement was carried out by ultraviolet spectroscopy (UV method (measurement wavelength: 343 nm)). The results are shown in FIG. 4. All pharmaceutical compositions showed improved dissolution properties in comparison with a pharmaceutical composition containing a crystalline drug.

<Experimental Example 3> Measurement of Related Substances

The pharmaceutical compositions for oral administration (tablets) of Examples 4, 8, and 9 were placed in aluminum bags, and allowed to stand at 70° C. for 7 days while sealing. The measurement of related substances before and after storage was carried out by an HPLC method.

The measurement of related substances was carried out under the following conditions:

As an HPLC column, Inertsil C8-3, particle size: 3 m, 4.6 mm (inner diameter)×15 cm (manufactured by GL Sciences), or its equivalent, was used, and maintained at a constant temperature of around 40° C.

As mobile phase A, a perchlorate solution (pH 2.0) was used.

As mobile phase B, acetonitrile was used.

As an eluent, an acetonitrile/water mixture (7:3) was used.

As sample solutions, samples were diluted with the eluent so that the concentration of compound A was 200 µg/mL.

The measurement of related substances was carried out using an ultraviolet absorption spectrophotometer (wavelength: 210 nm), in accordance with the gradient program shown in Table 4 below, and the percentage of the peak area of each related substance was calculated, as a percentage with respect to the total peak area of compound A and its related substances.

TABLE 4

| Time from injection (min.) | Mobile phase A (vol %) | Mobile phase B (vol %) |
| --- | --- | --- |
| 0 to 15 | 100 → 62 | 0 → 38 |
| 15 to 30 | 62 → 57 | 38 → 43 |
| 30 to 60 | 57 → 10 | 43 → 90 |
| 60 to 62 | 10 | 90 |
| 62 to 62.1 | 10 → 100 | 90 → 0 |
| 62.1 to 70 | 100 | 0 |

The results are shown in Table 5. In the pharmaceutical compositions of Examples 4, 8, and 9, the generation of related substances of compound A during storage was inhibited. In particular, the pharmaceutical composition of Example 9 inhibited the generation of related substances of compound A most strongly.

TABLE 5

| Percentage of maximum related substance (%) | Before storage | 70° C./ 7 days |
| --- | --- | --- |
| Example 4 | 0.34 | 0.81 |
| Example 8 | 0.35 | 0.65 |
| Example 9 | 0.34 | 0.52 |

<Experimental Example 4> Dissolution Stability

The pharmaceutical compositions for oral administration of Examples 8 and 9 of the present invention were allowed to stand at 25° C., 75% RH for 6 days under opened conditions. The dissolution properties before and after storage were evaluated in accordance with a Dissolution Test, a paddle method (50 rpm) of the Japanese Pharmacopoeia. As a test fluid, 0.03 N hydrochloric acid (900 mL) was used, and the dissolution rate of compound A after 30 minutes from the beginning of the test was measured by ultraviolet spectroscopy (UV method (measurement wavelength: 343 nm)). The results are shown in Table 6. In the pharmaceutical compositions of Examples 8 and 9, the change in dissolution rate of compound A could be inhibited.

TABLE 6

| | Dissolution rate after 30 min. (%) | |
| --- | --- | --- |
| | Before storage | 25° C. 75% RH/6 days |
| Example 8 | 90.6 | 88.8 |
| Example 9 | 99.0 | 94.3 |

<Experimental Example 5> Dissolution Stability

The pharmaceutical compositions for oral administration of Examples 12 to 22 of the present invention were allowed to stand at 25° C., 75% RH for 6 days under opened conditions. The dissolution properties before and after storage were evaluated in accordance with a Dissolution Test, a paddle method (50 rpm) of the Japanese Pharmacopoeia. As a test fluid, 0.03 N hydrochloric acid (900 mL) was used, and the dissolution rate of compound A after 15 minutes from the beginning of the test was measured by ultraviolet spectroscopy (UV method (measurement wavelength: 343 nm)). The results are shown in Table 7. In the pharmaceutical compositions of Examples 12 to 22, the change in dissolution rate of compound A could be inhibited.

TABLE 7

| | Dissolution rate after 15 min. (%) | |
| --- | --- | --- |
| | Before storage | 25° C. 75%RH/6 days |
| Example 12 | 91.9 | 94.1 |
| Example 13 | 92.6 | 93.1 |
| Example 14 | 96.5 | 89.9 |
| Example 15 | 92.0 | 91.5 |
| Example 16 | 94.1 | 90.5 |
| Example 17 | 93.5 | 88.4 |
| Example 18 | 98.1 | 91.6 |
| Example 19 | 96.6 | 91.3 |
| Example 20 | 94.7 | 91.3 |
| Example 21 | 82.8 | 88.2 |
| Example 22 | 88.1 | 92.5 |

Example 23

A spray solution was prepared by dissolving 50 g of compound A and 15 g of hydroxypropyl cellulose in a mixture of dichloromethane and methanol. The spray solution was dried by spray-drying to obtain a pharmaceutical composition for oral administration (solid dispersion) of the present invention.

Example 24

A spray solution was prepared by dissolving 500 g of compound A and 500 g of hydroxypropyl cellulose in a mixture of dichloromethane and methanol. The spray solution was dried by spray-drying to obtain a pharmaceutical composition for oral administration (solid dispersion) of the present invention.

Example 25

A spray solution was prepared by dissolving 50 g of compound A and 25 g of hypromellose in a mixture of dichloromethane and methanol. The spray solution was dried by spray-drying to obtain a pharmaceutical composition for oral administration (solid dispersion) of the present invention.

<Experimental Example 6> Dose Proportionality

Each of the pharmaceutical compositions (solid dispersions, corresponding to 100 mg or 500 mg of compound A) obtained in Examples 23 to 25 was orally administered to male beagle dogs in a fasted state. After the administration, blood was periodically collected, and the concentration of compound A in plasma obtained by centrifugation was measured. The dogs were made to fast 16 hours or more ahead of the scheduled administration time. Further, the dogs were subjected to pentagastrin treatment (intramuscular administration in the buttocks; 30 minutes before administration, and 30 and 90 minutes after administration) to control the intragastric pH to acidity, and the test was carried out. When the area under the plasma concentration time curve from the beginning of the oral administration to 24 hours ($AUC^{0-24h}$) of each pharmaceutical composition containing 100 mg of compound A was regarded as 1.00, the $AUC^{0-24h}$ of each pharmaceutical composition containing 500 mg of compound A was calculated as "$AUC^{0-24h}$ (GMR)". The results are shown in Table 8.

It was found that, in particular, the pharmaceutical compositions (solid dispersions) of Examples 23 and 24 exhibited good dose proportionality.

TABLE 8

|  | $AUC^{0-24h}$ (GMR) | |
| --- | --- | --- |
|  | 100 mg | 500 mg |
| Example 23 | 1.00 (N = 2) | 3.96 (N = 2) |
| Example 24 | 1.00 (N = 2) | 3.62 (N = 2) |
| Example 25 | 1.00 (N = 1) | 2.34 (N = 1) |

Number of dogs in parentheses

INDUSTRIAL APPLICABILITY

According to the pharmaceutical composition for oral administration of the present invention, the pharmaceutical composition comprising compound A or a pharmaceutically acceptable salt thereof, which is pH-dependent, can be rapidly disintegrated and dispersed. Further, a decrease in solubility caused by gelation and aggregation of the drug and/or a water-soluble polymer as a carrier for a solid dispersion can be avoided, and as a result, it can be expected that a decrease in absorbability accompanied by drug crystal precipitation due to a decrease in drug solubility in the small intestine pH range can be avoided.

Although the present invention has been described with reference to specific embodiments, various changes and modifications obvious to those skilled in the art are possible without departing from the scope of the appended claims.

The invention claimed is:

1. A pharmaceutical composition for oral administration, comprising a solid dispersion of 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}piperdine-4-carboxylic acid, or a pharmaceutically acceptable salt thereof, and a cellulose derivative, wherein the cellulose derivative is a member selected from the group consisting of hydroxypropyl cellulose, hypromellose and combinations thereof and wherein said cellulose derivative is present at about 20% to about 500% by weight relative to 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}piperdine-4-carboxylic acid, crystalline cellulose as a disintegrating agent, wherein said composition further comprises another disintegrating component which is one member selected from the group consisting of low-substituted hydroxypropyl cellulose, and croscarmellose sodium and wherein sodium starch glycolate is excluded from the composition.

2. The pharmaceutical composition for oral administration according to claim 1, wherein the cellulose derivative is hydroxypropyl cellulose.

3. The pharmaceutical composition for oral administration according to claim 1, further comprising an effervescent substance.

4. The pharmaceutical composition for oral administration according to claim 3, wherein the effervescent substance is sodium hydrogen carbonate.

5. The pharmaceutical composition for oral administration according to claim 1, wherein the other disintegrating component is low-substituted hydroxypropyl cellulose.

6. The pharmaceutical composition for oral administration according to claim 1, wherein the other disintegrating component is croscarmellose sodium.

7. The pharmaceutical composition for oral administration according to claim 1, wherein the pharmaceutical composition for oral administration is a tablet.

8. The pharmaceutical composition for oral administration according to claim 1, wherein the pharmaceutical composition for oral administration is a pharmaceutical composition for preventing and/or treating bladder or urinary tract diseases related to bladder contraction by a muscarinic M3 receptor.

* * * * *